United States Patent
Rao et al.

(10) Patent No.: US 8,394,963 B2
(45) Date of Patent: Mar. 12, 2013

(54) PROCESS FOR THE PREPARATION OF ESOMEPRAZOLE MAGNESIUM DIHYDRATE

(75) Inventors: Dharmaraj Ramachandra Rao, Thane (IN); Rajendra Narayanrao Kankan, Mumbai (IN); Srinivas Laxminarayan Pathi, Bangalore (IN); Gopalakrishna Sumana Bangalore, Bangalore (IN)

(73) Assignee: Cipla Limited, Mumbai (IN)

( * ) Notice: Subject to any disclaimer, the term of this patent is extended or adjusted under 35 U.S.C. 154(b) by 432 days.

(21) Appl. No.: 12/527,967

(22) PCT Filed: Feb. 21, 2008

(86) PCT No.: PCT/GB2008/000062
§ 371 (c)(1),
(2), (4) Date: Dec. 7, 2009

(87) PCT Pub. No.: WO2008/102145
PCT Pub. Date: Aug. 28, 2008

(65) Prior Publication Data
US 2010/0113526 A1    May 6, 2010

(30) Foreign Application Priority Data
Feb. 21, 2007 (IN) .......................... 348/MUM/2007

(51) Int. Cl.
*C07D 401/12* (2006.01)
(52) U.S. Cl. .................................. 546/273.7
(58) Field of Classification Search ............... 546/273.7
See application file for complete search history.

(56) References Cited

U.S. PATENT DOCUMENTS

| | | | |
|---|---|---|---|
| 4,255,431 A | 3/1981 | Junggren et al. | |
| 4,738,974 A | 4/1988 | Brandstrom | |
| 5,714,504 A | 2/1998 | Lindberg et al. | |
| 5,877,192 A | 3/1999 | Lindberg et al. | |
| 5,948,789 A | 9/1999 | Larsson et al. | |
| 6,369,085 B1 | 4/2002 | Cotton et al. | |
| 7,176,319 B2 | 2/2007 | Parthasaradhi Reddy et al. | |
| 7,365,206 B2 | 4/2008 | Parthasaradhi Reddy et al. | |
| 2003/0212274 A1 | 11/2003 | Vijayaraghavan et al. | |
| 2005/0267157 A1 | 12/2005 | White et al. | |

FOREIGN PATENT DOCUMENTS

| | | |
|---|---|---|
| DE | 4035455 A1 | 5/1992 |
| EP | 0005129 A1 | 10/1979 |
| EP | 0897386 B1 | 8/2002 |
| EP | 0773940 B1 | 6/2003 |
| WO | 9427988 A1 | 12/1994 |
| WO | 9602535 A1 | 2/1996 |
| WO | 9854171 A1 | 12/1998 |
| WO | 0027841 A1 | 5/2000 |
| WO | 0187831 A2 | 11/2001 |
| WO | 03062223 A1 | 7/2003 |
| WO | 2004002982 A2 | 1/2004 |
| WO | 2004/020436 | * 3/2004 |
| WO | 2004037253 A1 | 5/2004 |
| WO | 2004046134 A2 | 6/2004 |
| WO | 2005023797 A1 | 3/2005 |
| WO | 2005116011 A1 | 12/2005 |
| WO | 2006096709 A2 | 9/2006 |
| WO | 2008102145 A2 | 8/2008 |
| WO | 2008102145 A3 | 8/2008 |

OTHER PUBLICATIONS

Khiar, Noureddine, et al., "Dynamic Kinetic Transformation of Sulfinyl Chlorides: Synthesis of Enantiomerically Pure C2-Symmetric Bis-Sulfoxides," J. Org. Chem, 2002, vol. 67, pp. 345-356, American Chemical Society.

Foreign communication from the priority application—International Search Report and Written Opinion, PCT/GB2008/000602, Sep. 25, 2008, 15 pages.

Foreign communication from a related application—European Search Report, Application 09178721.8, Mar. 25, 2010, 6 pages.

Foreign communication from the priority application—International Preliminary Report on Patentability, PCT/GB2008/000602, Aug. 26, 2009, 9 pages.

Kagan, Henri B., "Asymmetric Oxidation of Sulfides," Chapter 4.3, Catalytic Asymmetric Synthesis, pp. 203-226 plus 2 pages, Iwao Ojima, Editor, 1993, VCH Publishers, Inc.

Madesclaire, Michel, "Synthesis of Sulfoxides by Oxidation of Thioethers," Tetrahedron Report No. 210, Tetrahedron, 1986, vol. 42, No. 20, pp. 5459-5495, Pergamon Journals Ltd, Great Britain.

Pitchen, P., et al., "An efficient Asymmetric Oxidation of Sulfides to Sulfoxides," J. Am. Chem. Soc., 1984, vol. 106, pp. 8188-8193, American Chemical Society.

Procter, David J., "The synthesis of thiols, selenols, sulfides, selenides, sulfoxides, selenoxides, sulfones and selenones," J. Chem. Soc., Perkins Trans 1, 2000, pp. 835-871, Royal Society of Chemistry.

* cited by examiner

*Primary Examiner* — Patricia L. Morris
(74) *Attorney, Agent, or Firm* — Conley Rose, P.C.; Rodney B. Carroll

(57) ABSTRACT

A process for preparing Form A of (S)-5-methoxy-2-[[(4-methoxy-3,5-dimethyl-2-pyridinyl) -methyl]sulfinyl]-1H-benzimidazole magnesium dihydrate, processes for preparing various intermediates useful in the preparation of Form A of (S)-5-methoxy-2-[[(4-methoxy-3,5-dimethyl-2-pyridinyl)-methyl]sulfinyl]-1H-benzimidazole magnesium dihydrate and a novel polymorphic Form II of 5-methoxy-2-[[(4-methoxy-3,5-dimethyl-2-pyridinyl)-methyl]thio]-1H-benzimidazole.

8 Claims, 3 Drawing Sheets

PROCESS FOR THE PREPARATION OF ESOMEPRAZOLE MAGNESIUM DIHYDRATE

CROSS-REFERENCE TO RELATED APPLICATIONS

This application is a filing under 35 U.S.C. 371 of International Application No. PCT/GB2008/000602 filed Feb. 21, 2008, entitled "Process for the Preparation of Esomeprazole Magnesium Dihydrate," claiming priority of Indian Patent Application No. 348/MUM/2007 filed Feb. 21, 2007, which applications are incorporated by reference herein in their entirety.

FIELD OF THE INVENTION

The present invention relates to an improved process for the preparation of polymorphic Form A of (S)-5-methoxy-2-[[(4-methoxy-3,5-dimethyl-2-pyridinyl)-methyl]sulfinyl]-1H-benzimidazole magnesium dihydrate i.e. esomeprazole magnesium dihydrate, a novel polymorph of the intermediate 5-methoxy-2-[[(4-methoxy-3,5-dimethyl-2-pyridinyl)-methyl]thio]-1H-benzimidazole and its synthesis.

BACKGROUND OF THE INVENTION

Omeprazole is chemically termed as 5-methoxy-2-[[(4-methoxy-3,5-dimethyl-2-pyridinyl)-methyl]sulfinyl]-1H-benzimidazole. The S-enantiomer is chemically known as (S)-5-methoxy-2-[[(4-methoxy-3,5-dimethyl-2-pyridinyl)-methyl]sulfinyl}-1H-benzimidazole and hence named "esomeprazole." The magnesium salt of esomeprazole is represented by formula I.

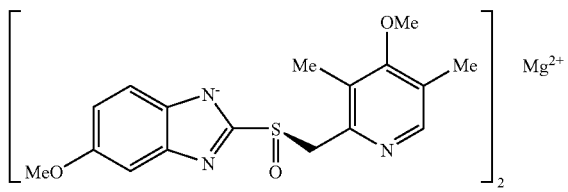

I

Esomeprazole is a proton pump inhibitor used in the treatment of dyspepsia, peptic ulcer disease, gastroesophageal reflux disease and Zollinger-Ellison syndrome. Esomeprazole is the S-enantiomer of omeprazole (marketed as Losec/Prilosec).

A process for asymmetric oxidation of sulphides to sulfoxides has been developed by Kagan and co-workers (J. Am. Chem. Soc. 1984; 106, 8188-8193), the oxidation is performed by using tert-butyl hydroperoxide (TBHP) as oxidizing agent in the presence of one equivalent of a chiral complex.

Various metal catalysed enantioselective oxidations or stoichiometric transition-metal-promoted reactions are described in the literature to prepare chiral sulfoxides by oxidation of the corresponding sulphides (Kagan H. B. In Catalytic Asymmetric Synthesis; Madesclaire M. Tetrahedron 1986; 42, 5459-5495; Procter D. J. Chem. Soc Perkin Trans 2000; 835-871; Khiar, N. J. Org. Chem. 2002, 67, 345). Metal catalysed enantioselective oxidations involve a metal catalyst complexed with a chiral ligand such as diethyl tartrate, trialkanolamine titanium (IV) complex, zirconium (IV) complexes etc. in the presence of various oxidants.

Omeprazole and therapeutically acceptable salts thereof, are first disclosed in EP 5129 and U.S. Pat. No. 4,255,431. The specific alkaline salts of omeprazole are also disclosed in U.S. Pat. Nos. 4,738,974, 5,714,504 and 5,877,192.

The resolution processes of racemates of omeprazole are for example disclosed in DE 4035455 and WO 94/27988.

An enantioselective synthesis of omeprazole by asymmetric oxidation is reported in WO 96/02535 (equivalent patents U.S. Pat. No. 5,948,789 and EP 0773940), which claims a process for enantioselective synthesis of the sulphoxide either as a single enantiomer or in an enantiometrically enriched form characterized in that a pro-chiral sulphide is oxidized in an organic solvent with an oxidizing agent in the presence of a chiral titanium complex optionally in the presence of a base, wherein the titanium complex has been prepared in the presence of the pro-chiral sulphide. From the description and the examples of the patent it is clearly understood that the absence of base yields a product having low enantiomeric purity as shown in examples 7 and 8. An excess enantioselectivity is obtained due to the presence of base in the reaction and preparation of the chiral complex in the presence of the pro-chiral sulphide. Examples 6, 7, 8, A, B and C in WO 96/02535 disclose processes for preparing the sulphoxide in the absence of a base. The amount of desired sulphoxide produced in the exemplified processes ranges from 22 to 31%.

Preparations of optically pure sulfoxides are claimed in WO 04/02982. The patent discloses a method of forming transition metal complexes at acid sulfoxide group which is reacted with a chiral acid to form an addition product, followed by separation.

U.S. Pat. No. 6,369,085 discloses various forms of esomeprazole magnesium trihydrate and dihydrate prepared from the corresponding potassium salt.

EP 0897386 claims a process for the preparation of the magnesium salt of esomeprazole comprising direct conversion of the sulphoxide to the magnesium salt in the presence of an organic base with a $pK_a$ from 7-12 and a magnesium source.

WO 04/046134 discloses crystalline Form II of esomeprazole magnesium trihydrate.

Amorphous esomeprazole magnesium and a process for its preparation are disclosed in patents WO 01/87831, WO 2004037253, US 2003-212274 and WO 06/96709.

WO 05/23797 discloses novel salts of R and S omeprazole.

US 2006-0089386 discloses a process in which sulfoxide derivatives are treated with a chiral acid such as camphor sulfonyl chloride followed by fractional crystallization, deprotection and conversion to a salt.

A similar method is also disclosed in WO 05/116011 and US 2006-166986 in which benzimidazole sulfide derivatives are reacted with a chiral acid reagent, oxidized, followed by separation of diastereomers, finally deprotection.

U.S. Pat. No. 6,369,085 discloses esomeprazole magnesium dihydrate Form A and B. The process for preparation of esomeprazole magnesium dihydrate Form A is not industrially efficient as it often results in the dihydrate being converted to the trihydrate or amorphous esomeprazole magnesium. This process is disadvantageous as the polymorph A of the dihydrate cannot be obtained consistently as the wet dihydrate gets converted during drying to the trihydrate or amorphous form. Use of acetone to slurry the product and dry, results in an inconsistent polymorph.

Hence there is a need for a robust process for the synthesis of esomeprazole magnesium dihydrate in good yield consistently on a large scale and in a reproducible manner. The present invention provides an industrially suitable process for preparation of esomeprazole magnesium dihydrate. More particularly Form A of esomeprazole magnesium dihydrate.

OBJECTIVES OF THE INVENTION

The object of the present invention is to provide an improved process for the preparation of esomeprazole magnesium dihydrate Form A from oxidizing the intermediate, 5-methoxy-2-[[(4-methoxy-3,5-dimethyl-2-pyridinyl)-methyl]thio]-1H-benzimidazole.

Another object of the present invention is to provide an improved process for the preparation of esomeprazole magnesium dihydrate Form A by oxidizing a novel polymorph of intermediate, 5-methoxy-2[[(4-methoxy-3,5-dimethyl-2-pyridinyl)-methyl]thio]-1H-benzimidazole.

Another object of the present invention is to provide a consistent process for the preparation of esomeprazole magnesium dihydrate Form A on a large scale.

Another object of the present invention is to provide a process for the preparation of a novel polymorph of 5-methoxy-2[[(4-methoxy-3,5-dimethyl-2-pyridinyl)-methyl]thio]-1H-benzimidazole.

Yet another object of the present invention is to provide pharmaceutical compositions comprising a polymorphic form of esomeprazole magnesium dihydrate prepared using the novel processes.

Yet another object of the present invention is to provide therapeutic uses and therapeutic methods of treatment employing compositions comprising a polymorphic form of esomeprazole magnesium dihydrate.

SUMMARY OF THE INVENTION

According to a first aspect of the present invention, there is provided Form II of 5-methoxy-2-[[(4-methoxy-3,5-dimethyl-2-pyridinyl)-methyl]thio]-1H-benzimidazole. In an embodiment, there is provided Form II of 5-methoxy-2-[[(4-methoxy-3,5-dimethyl-2-pyridinyl)-methyl]thio]-1H-benzimidazole, having an XRPD pattern with °2θ values at 20.7, 20.9 and 25.6±0.2°2θ. The XRPD pattern may have further peaks at 8.1, 23.0, 25.7 and 29.0°2θ±0.2°2θ. In an embodiment, there is provided Form II of 5-methoxy-2-[[(4-methoxy-3,5-dimethyl-2-pyridinyl)-methyl]thio]-1H-benzimidazole, having the XRPD pattern as shown in FIG. 2.

According to another aspect of the present invention, there is provided a process for preparing Form II of 5-methoxy-2-[[(4-methoxy-3,5-dimethyl-2-pyridinyl)-methyl]thio]-1H-benzimidazole comprising crystallising or recrystallising crude 5-methoxy-2-[[(4-methoxy-3,5-dimethyl-2-pyridinyl)-methyl]thio]-1H-benzimidazole from ethyl acetate, cooling and isolating the Form II of 5-methoxy-2-[[(4-methoxy-3,5-dimethyl-2-pyridinyl)-methyl]thio]-1H-benzimidazole. In an embodiment, the crystallisation or recrystallisation from ethyl acetate is carried out at a temperature ranging from 40° C. to 70° C., preferably 50° C. to 60° C. In an embodiment, the cooling is to a temperature ranging from −10° C. to −5° C. Suitably, the isolation comprises filtration followed by washing with ethyl acetate. Optionally, the washed Form II of 5-methoxy-2-[[(4-methoxy-3,5-dimethyl-2-pyridinyl)-methyl]thio]-1H-benzimidazole is dried at a temperature ranging from 30° C. to 35° C. In an embodiment, the crude 5-methoxy-2-[[(4-methoxy-3,5-dimethyl-2-pyridinyl)-methyl]thio]-1H-benzimidazole is extracted with a suitable organic solvent, such as methylene dichloride, before recrystallisation.

Suitably, the crude 5-methoxy-2-[[(4-methoxy-3,5-dimethyl-2-pyridinyl)-methyl]thio]-1H-benzimidazole is prepared by condensing 2-chloromethyl-3,5-dimethyl-4-methoxy pyridine hydrochloride and 2-mercapto-5-methoxy benzimidazole. The condensation may be carried out in the presence of a catalyst such as tetrabutyl ammonium bromide. The condensation may be carried out under basic conditions.

In an embodiment, the 2-chloromethyl-3,5-dimethyl-4-methoxy pyridine hydrochloride is prepared by converting 2-hydroxymethyl-3,5-dimethyl-4-methoxy pyridine hydrochloride to 2-chloromethyl-3,5-dimethyl-4-methoxy pyridine. The 2-hydroxymethyl-3,5-dimethyl-4-methoxy pyridine hydrochloride may be converted to 2-chloromethyl-3,5-dimethyl-4-methoxy pyridine by reaction with a chlorinating agent such as thionyl chloride. The chlorination may be carried out in a suitable organic solvent such as methylene chloride, chloroform or ethylene chloride, preferably methylene chloride. In an embodiment, the chlorination is carried out at a temperature ranging from 10° C. to 25° C.

According to another aspect of the present invention, there is provided a process for preparing (S)-5-methoxy-2-[[(4-methoxy-3,5-dimethyl-2-pyridinyl)-methyl]sulfinyl]-1H-benzimidazole comprising oxidising 5-methoxy-2-[[(4-methoxy-3,5-dimethyl-2-pyridinyl)-methyl]thio]-1H-benzimidazole in the absence of a base, the oxidising comprising the steps of preparing a chiral titanium complex, reacting the chiral titanium complex with 5-methoxy-2-[[(4-methoxy-3,5-dimethyl-2-pyridinyl)-methyl]thio]-1H-benzimidazole and adding an oxidising agent. Preferably, the oxidising agent is added to the reaction mixture at a temperature ranging from 5° C. to 20° C., preferably 10° C. to 15° C. In an embodiment, the chiral titanium complex is prepared from D-(−)-diethyl tartrate and titanium (IV) isopropoxide. Preferably, the temperature of the reaction mixture during the preparation of the chiral titanium complex ranges from 20° C. to 35° C., preferably 25° C. to 30° C. Preferably, the temperature of the reaction mixture during the step of reacting the chiral titanium complex with 5-methoxy-2-[[(4-methoxy-3,5-dimethyl-2-pyridinyl)-methyl]thio]-1H-benzimidazole ranges from 60° C. to 80° C., preferably 70° C. to 75° C. In an embodiment, the oxidising agent is an organic peroxide, preferably cumene hydroperoxide. The oxidising steps may be carried out in the presence of an organic solvent. Suitably, the solvent is toluene or dichloromethane. Preferably, the solvent is toluene. Preferably, the reaction mixture is not stirred after addition of the oxidising agent.

In an embodiment, the 5-methoxy-2-[[(4-methoxy-3,5-dimethyl-2-pyridinyl)-methyl]thio]-1H-benzimidazole is polymorphic Form I or polymorphic Form II. Preferably, the 5-methoxy-2-[[(4-methoxy-3,5-dimethyl-2-pyridinyl)-methyl]thio]-1H-benzimidazole is polymorphic polymorphic Form II. The Form II of 5-methoxy-2-[[(4-methoxy-3,5-dimethyl-2-pyridinyl)-methyl]thio]-1H-benzimidazole may be prepared by the process described above.

In an embodiment, the (S)-5-methoxy-2-[[(4-methoxy-3,5-dimethyl-2-pyridinyl) -methyl]sulfinyl]-1H-benzimidazole as prepared by the process described above is converted to a salt thereof. Suitably, the salt is an alkali metal salt. Preferably, the alkali metal salt is the potassium salt. The (S)-5-methoxy-2-[[(4-methoxy-3,5-dimethyl-2-pyridinyl)-methyl]sulfinyl]-1H-benzimidazole may be converted to the potassium salt in the presence of a potassium source, such as methanolic potassium hydroxide (i.e. a solution of potassium hydroxide in methanol), methanolic potassium methoxide (i.e. a solution of potassium methoxide in methanol) or ethanolic potassium hydroxide (i.e. a solution of potassium hydroxide in ethanol). Preferably, the potassium source is methanolic potassium hydroxide. The conversion to the potassium salt may be carried out at a temperature below 40° C. Suitably, the conversion is carried out for a period of time less than 5 hours, more preferably less than 3 hours. Optionally, the salt of (S)-5-methoxy-2-[[(4-methoxy-3,5-dimethyl-2-pyridinyl)-methyl]sulfinyl]-1H-benzimidazole may be purified, for example by recrystallisation. The recrystallisation may be from acetone and methanol.

In an embodiment, the salt of (S)-5-methoxy-2-[[(4-methoxy-3,5-dimethyl-2-pyridinyl)-methyl]sulfinyl]-1H-benzimidazole is converted to (S)-5-methoxy-2-[[(4-methoxy-3,5-dimethyl-2-pyridinyl)-methyl]sulfinyl]-1H-benzimidazole magnesium dihydrate in the presence of a magnesium source, such as magnesium chloride hexahydrate or magnesium sulphate. Preferably, the magnesium source is magnesium chloride hexahydrate. In an embodiment, the conversion to the magnesium salt is carried out in the absence of an organic base. Suitably, the conversion to the magnesium salt is carried out in an organic solvent, such as methanol, ethanol, denatured spirit, isopropyl alcohol or dimethyl formamide. Optionally, the salt of (S)-5-methoxy-2-[[(4-methoxy-3,5-dimethyl-2-pyridinyl)-methyl]sulfinyl]-1H-benzimidazole may be purified before being converted to the magnesium dihydrate, for example by recrystallisation. The recrystallisation may be from acetone and methanol.

According to another aspect of the present invention, there is provided a process for preparing Form A of (S)-5-methoxy-2-[[(4-methoxy-3,5-dimethyl-2-pyridinyl)-methyl]sulfinyl]-1H-benzimidazole magnesium dihydrate comprising crystallising or recrystallising crude (S)-5-methoxy-2-[[(4-methoxy-3,5-dimethyl-2-pyridinyl)-methyl]sulfinyl]-1H-benzimidazole magnesium dihydrate in the presence of ethyl acetate.

Surprisingly, it has been found that the use of ethyl acetate during recrystallisation of crude Form A of magnesium dihydrate, and optionally stiffing the product after recrystallisation, consistently results in Form A of magnesium dihydrate in very high yield. The process can be easily carried out on the laboratory scale as well as industrial scale.

In an embodiment, the crystallisation or recrystallisation is initiated by the addition of a solvent comprising ethyl acetate to the crude (S)-5-methoxy-2-[[(4-methoxy-3,5-dimethyl-2-pyridinyl)-methyl]sulfinyl]-1H-benzimidazole magnesium dihydrate. In an embodiment, the solvent is an ethyl acetate-water mixture. Preferably, the crystallisation or recrystallisation reaction mixture is stirred for a period of time ranging from 10 minutes to 3 hours, preferably the crystallisation or recrystallisation reaction mixture is stirred for a period of time ranging from 15 minutes to 1 hour, more preferably the crystallisation or recrystallisation reaction mixture is stirred for a period of time ranging from 15 minutes to 30 minutes. The product of the crystallisation or recrystallisation may be filtered and washed with ethyl acetate. The crystallised or recrystallised Form A of (S)-5-methoxy-2-[[(4-methoxy-3,5-dimethyl-2-pyridinyl) -methyl]sulfinyl]-1H-benzimidazole magnesium dihydrate may be dried at a temperature below 75° C. under vacuum.

In an embodiment, the crude (S)-5-methoxy-2-[[(4-methoxy-3,5-dimethyl-2-pyridinyl)-methyl]sulfinyl]-1H-benzimidazole magnesium dihydrate is prepared according to a process described above.

According to another aspect of the present invention, there is provided Form A of (S)-5-methoxy-2-[[(4-methoxy-3,5-dimethyl-2-pyridinyl)-methyl]sulfinyl]-1H-benzimidazole magnesium dihydrate prepared according to a process as described above.

According to yet another aspect of the present invention, there is provided a pharmaceutical composition comprising Form A of (S)-5-methoxy-2-[[(4-methoxy-3,5-dimethyl-2-pyridinyl)-methyl]sulfinyl]-1H-benzimidazole magnesium dihydrate as described above together with one or more pharmaceutically acceptable excipients.

According to yet another aspect of the present invention, there is provided the use of Form A of (S)-5-methoxy-2-[[(4-methoxy-3,5-dimethyl-2-pyridinyl)-methyl]sulfinyl]-1H-benzimidazole magnesium dihydrate as described above in medicine.

According to a still further aspect of the present invention, there is provided the use of Form A of (S)-5-methoxy-2-[[(4-methoxy-3,5-dimethyl-2-pyridinyl)-methyl]sulfinyl]-1H-benzimidazole magnesium dihydrate as described above in the treatment of dyspepsia, peptic ulcer disease, gastroesophageal reflux disease or Zollinger-Ellison syndrome.

According to a still further aspect of the present invention, there is provided the use of Form A of (S)-5-methoxy-2-[[(4-methoxy-3,5-dimethyl-2-pyridinyl)-methyl]sulfinyl]-1H-benzimidazole magnesium dihydrate as described above in the manufacture of a medicament for the treatment of dyspepsia, peptic ulcer disease, gastroesophageal reflux disease or Zollinger-Ellison syndrome.

According to another aspect of the present invention, there is provided a method of treating dyspepsia, peptic ulcer disease, gastroesophageal reflux disease or Zollinger-Ellison syndrome comprising administering to a patient in need thereof. Form A of (S)-5-methoxy-2-[[(4-methoxy-3,5-dimethyl-2-pyridinyl)-methyl]sulfinyl]-1H-benzimidazole magnesium dihydrate as described above.

DETAILED DESCRIPTION

Figure 1:
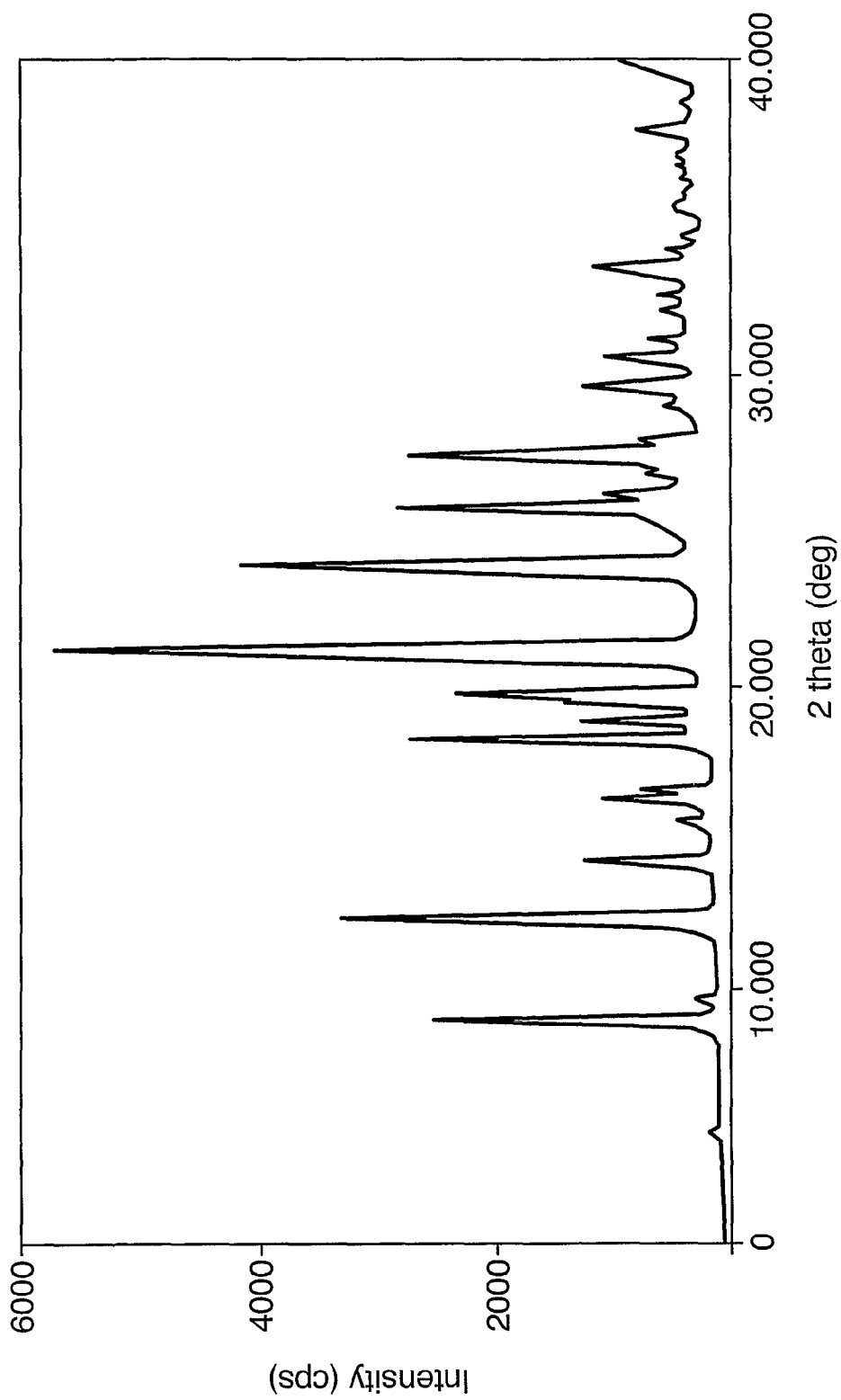
FIG. 1 shows the X-ray powder diffractogram of Form I of 5-methoxy-2-[[(4-methoxy-3,5-dimethyl-2-pyridinyl)-methyl]thio]-1H-benzimidazole.
Figure 2:
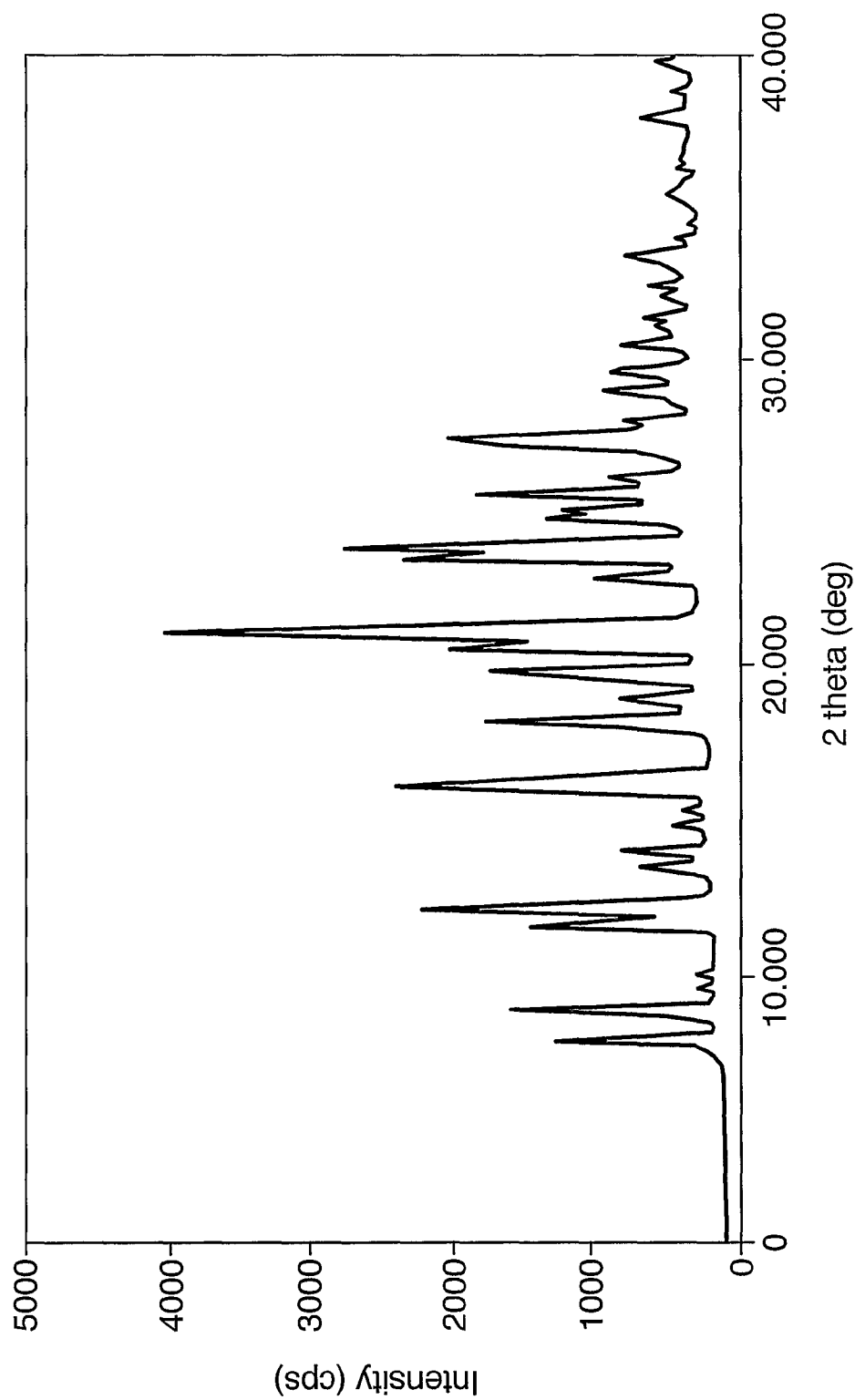
FIG. 2 shows the X-ray powder diffractogram of Form II of 5-methoxy-2-[[(4-methoxy-3,5-dimethyl-2-pyridinyl)-methyl]thio]-1H-benzimidazole.

Various processes given in the prior art for the synthesis of esomeprazole involve the use of a base, but the synthesis of esomeprazole magnesium dihydrate Form A using a base is inconsistent and non-reproducible.

5-methoxy-2-[[(4-methoxy-3,5-dimethyl-2-pyridinyl)-methyl]thio]-1H-benzimidazole is the key intermediate in the synthesis of esomeprazole. Surprisingly it was found that the key intermediate of esomeprazole exists in two polymorphic forms. By repeating the process as disclosed in EP5129, the crystals of the intermediate are isolated from ethanol and the resulting poylmorph hereinafter is termed as Form I.

Polymorphs of a compound differ in physical properties such as crystal structure, dissolution and particle size. Surprisingly it has been found that the two polymorphic forms of the thio intermediate 5-methoxy-2-[[(4-methoxy-3,5-dimethyl-2-pyridinyl)-methyl]thio]-1H-benzimidazole (compound III) have different reactivity: Form II, is found to be less soluble than Form I. Thus, the subsequent oxidation reaction using the Form II thio intermediate (compound III) is controlled, thereby fewer sulphone impurities N-oxide impurities and sulphone-N-oxide impurities are formed, which results in higher yield and higher enantioselectivity compared to the corresponding oxidation using Form I of thio intermediate (compound III). The comparison of solubility of Form I and Form II is given in Table 1.

TABLE 1

Solubility checked using 0.1 g of the sample at 25-30° C.

| Solvent | Form I | Form II |
|---|---|---|
| Acetone | 2.0 ml | 4.6 ml |
| Ethyl acetate | 4.6 ml | 12.0 ml |
| Toluene | 8.4 ml | 15.0 ml |
| Isopropyl acetate | 10.0 ml | 13.0 ml |

The present invention provides a new polymorphic form of the key intermediate of esomeprazole hereinafter termed as Form II. We have found that Form II is less reactive than Form I. This less reactive polymorphic Form II of the present invention can be easily converted to esomeprazole in good yield under the reaction conditions of the present invention.

The Form II of the present invention can be easily oxidized with an oxidizing agent such as cumene hydroperoxide and a chiral titanium complex, in the absence of base in good yields.

In one embodiment, the present invention provides, as depicted in scheme I, a novel process for the preparation of esomeprazole magnesium dihydrate using the novel polymorph Form II of intermediate 5-methoxy-2-[[(4-methoxy-3,5-dimethyl-2-pyridinyl)-methyl]thio]-1H-benzimidazole.

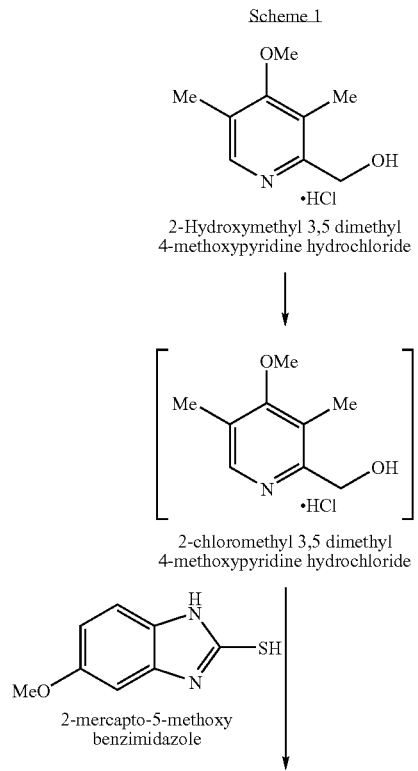

Scheme 1

2-Hydroxymethyl 3,5 dimethyl 4-methoxypyridine hydrochloride 2-chloromethyl 3,5 dimethyl 4-methoxypyridine hydrochloride 2-mercapto-5-methoxy benzimidazole

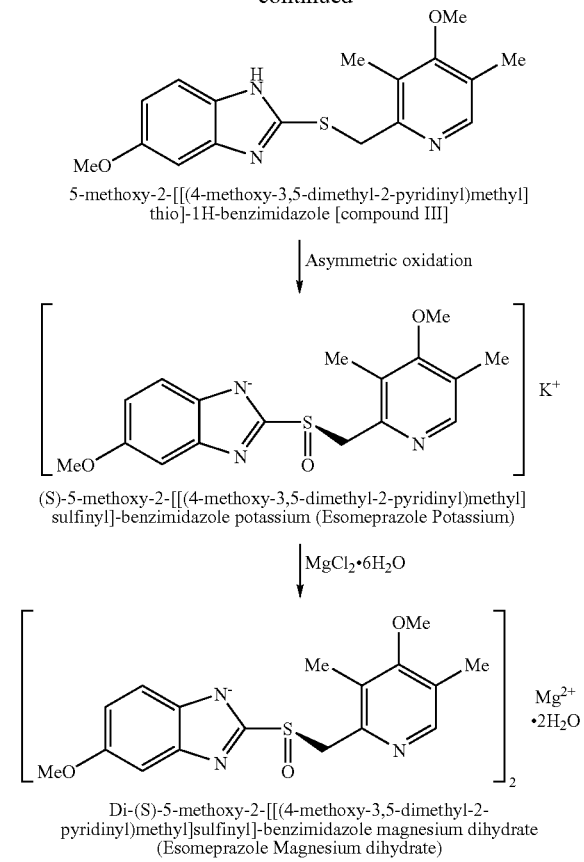

5-methoxy-2-[[(4-methoxy-3,5-dimethyl-2-pyridinyl)methyl]thio]-1H-benzimidazole [compound III]

Asymmetric oxidation (S)-5-methoxy-2-[[(4-methoxy-3,5-dimethyl-2-pyridinyl)methyl]sulfinyl]-benzimidazole potassium (Esomeprazole Potassium)

$MgCl_2 \cdot 6H_2O$

Di-(S)-5-methoxy-2-[[(4-methoxy-3,5-dimethyl-2-pyridinyl)methyl]sulfinyl]-benzimidazole magnesium dihydrate (Esomeprazole Magnesium dihydrate)

The embodiment shown in Scheme 1 involves conversion of 2-hydroxymethyl-3,5-dimethyl-4-methoxy pyridine hydrochloride to 2-chloromethyl-3,5-dimethyl-4-methoxy pyridine hydrochloride, which is further converted to 5-methoxy-2-[[(4-methoxy-3,5-dimethyl-2-pyridinyl)-methyl] thio]-1H-benzimidazole by reacting with 2-mercapto-5-methoxy benzimidazole and isolating as Form II. This polymorphic Form II may then converted to a salt of esomeprazole by asymmetric oxidation and may finally be converted to esomeprazole magnesium dihydrate.

In another embodiment, Form II of 5-methoxy-2[[(4-methoxy-3,5-dimethyl-2-pyridinyl)-methyl]thio]-1H-benzimidazole which is formed as an intermediate is oxidized with an oxidizing agent such as cumene hydroperoxide and a chiral titanium complex, in the absence of a base. The oxidation may be carried out in an organic solvent such as toluene or dichloromethane, more preferably toluene at a temperature below 25° C. and may be converted to the corresponding potassium salt by treatment with a potassium source, such as methanolic potassium hydroxide, methanolic potassium methoxide, ethanolic potassium hydroxide, more preferably methanolic potassium hydroxide, at a temperature below 40° C. for a duration of less than 5 hours, more preferably less than 3 hours. The process is reproducible industrially.

In another embodiment, the esomeprazole magnesium dihydrate Form A is prepared in a consistent manner by conversion of the salt of esomeprazole, for example the potassium salt, to the corresponding magnesium salt in a polymorphic Form A by treatment with a magnesium source, such as magnesium chloride hexahydrate, magnesium sulphate, more preferably magnesium chloride hexahydrate, in the absence of any organic base in an organic solvent such as methanol, denatured spirit, isopropyl alcohol, dimethyl formamide, more preferably methanol and denatured spirit. The solution is filtered, distilled and the precipitation is initialized by addition of an anti-solvent such as an ethyl acetate-water mixture. The product is filtered and washed with ethyl acetate during isolation after the crude isolation, or stirred for a period of time sufficient to facilitate formation of Form A after the crude isolation followed by drying under vacuum to give Form A in an extremely reproducible manner in the laboratory and on a large scale application. The time taken for stirring may range from 15 minutes to 3 hours, preferably 15 minutes to 1 hour, most preferably 15 minutes to 30 minutes.

The product so isolated is dried at elevated temperature, for example at a temperature below 75° C., under vacuum to obtain the desired polymorphic form of esomeprazole magnesium dihydrate i.e. Form A.

Esomeprazole can also be prepared from Form I of 5-methoxy-2-[[(4-methoxy-3,5-dimethyl-2-pyridinyl)-methyl]thio]-1H-benzimidazole using the above conditions but the yields are lower with low enantiomeric purity as more sulphone impurity forms due to its higher solubility in solvent which makes it more reactive.

In another embodiment, the process for the preparation of 5-methoxy-2-[[(4-methoxy-3,5-dimethyl-2-pyridinyl)-methyl]thio]-1H-benzimidazole Form II comprises treating 2-hydroxymethyl-3,5-dimethyl-4-methoxy pyridine hydrochloride with thionyl chloride in a suitable organic solvent such as methylene chloride, chloroform, ethylene chloride etc, preferably methylene chloride, at a temperature ranging from 10 to 25° C. The reaction mass containing 2-chloromethyl-3,5-dimethyl-4-methoxy pyridine hydrochloride is further reacted with 2-mercapto-5-methoxy benzimidazole in the presence of a catalyst like tetrabutyl ammonium bromide in basic conditions. After reaction completion, the organic layer is separated, extracted with methylene chloride, organic layer is washed with water, concentrated and stripped off with ethyl acetate. Further ethyl acetate is added, heated to 50 to 60° C. and chilled. The resulting solid is filtered and washed with chilled ethyl acetate. The solid obtained is dried at 30 to 35° C. to obtain Form II of 5-methoxy-2-[[(4-methoxy-3,5-dimethyl-2-pyridinyl)-methyl]thio]-1H-benzimidazole.

The polymorphic Forms I and II of the intermediate 5-methoxy-2-[[(4-methoxy-3,5-dimethyl-2-pyridinyl)-methyl]thio]-1H-benzimidazole are characterised by X-ray diffractogram and can be distinguished by their characteristic X-ray powder diffraction patterns indicating diffraction angles (i.e. degree 2θ) and relative intensities (i.e. % $I/I_o$) provided in Table II below.

The XRPD was measured on a Rigaku Miniflex X-ray powder diffractometer.

TABLE II

| Form I | | Form II | |
|---|---|---|---|
| Degrees 2θ | % $I/I_o$ | Degrees 2θ | % $I/I_o$ |
| 9.110 | 45 | 8.100 | 32 |
| 9.720 | 6 | 9.110 | 40 |
| 11.920 | 11 | 9.750 | 7 |
| 12.430 | 59 | 10.150 | 7 |
| 14.200 | 22 | 11.980 | 37 |
| 15.490 | 9 | 12.430 | 55 |
| 16.220 | 20 | 13.700 | 17 |
| 16.510 | 13 | 14.210 | 21 |
| 16.580 | 14 | 14.990 | 12 |
| 18.320 | 48 | 15.450 | 10 |
| 18.950 | 22 | 16.290 | 60 |
| 19.600 | 27 | 16.570 | 19 |
| 19.890 | 41 | 17.920 | 15 |
| 21.120 | 58 | 18.310 | 43 |
| 21.370 | 100 | 18.950 | 20 |
| 23.870 | 44 | 19.540 | 24 |
| 24.060 | 73 | 19.880 | 43 |
| 25.000 | 10 | 20.680 | 50 |
| 25.220 | 12 | 20.930 | 42 |
| 25.810 | 50 | 21.110 | 58 |
| 26.260 | 19 | 21.360 | 100 |
| 26.950 | 13 | 23.000 | 25 |
| 27.380 | 29 | 23.690 | 58 |
| 27.470 | 35 | 24.050 | 69 |
| 27.650 | 48 | 24.980 | 33 |
| 27.980 | 14 | 25.230 | 30 |
| 28.090 | 14 | 25.690 | 41 |
| 29.150 | 10 | 25.790 | 45 |
| 29.250 | 10 | 26.260 | 22 |
| 29.640 | 16 | 26.420 | 17 |
| 29.810 | 22 | 27.010 | 15 |
| 30.650 | 19 | 27.380 | 44 |
| 30.760 | 15 | 27.640 | 50 |
| 31.240 | 13 | 28.060 | 20 |
| 32.120 | 10 | 28.170 | 19 |
| 32.230 | 10 | 29.040 | 22 |
| 32.610 | 11 | 29.160 | 23 |
| 33.580 | 20 | 29.750 | 22 |
| 37.980 | 14 | 29.840 | 21 |
| | | 30.610 | 20 |
| | | 31.540 | 16 |
| | | 32.560 | 15 |
| | | 33.570 | 20 |
| | | 33.680 | 15 |
| | | 37.930 | 16 |

EXAMPLES

The details of the invention are given in the examples which are provided below for illustration only and therefore these examples should not be construed to limit the scope of the invention.

Reference Example 1 (According to EP5129)

Preparation of 5-methoxy-2-[[(4-methoxy-3,5-dimethyl-2-pyridinyl)-methyl)thio]-1H-benzimidazole Form I 2-chloromethyl-3,5-dimethyl-4-methoxy pyridine hydrochloride (25 g) and 2-mercapto-5-methoxy benzimidazole (20 g) were dissolved in 95% ethanol (200 ml). To this sodium hydroxide solution (8 g of sodium hydroxide dissolved in 20 ml of water) was added and refluxed for 2 hours. The sodium chloride formed was filtered off and the solution was concentrated to residue. The residue was then recrystallised from 70% of ethanol (30 ml) to yield 5-methoxy-2-[[(4-methoxy-3,5-dimethyl-2-pyridinyl)-methyl)thio]-1H-benzimidazole Form I (7 g).

Example 2

Preparation of 5-methoxy-2-[[(4-methoxy-3,5-dimethyl-2-pyridinyl)-methyl)thio]-1H-benzimidazole Form I 2-chloromethyl-3,5-dimethyl-4-methoxy pyridine hydrochloride (50 g) and 2-mercapto-5-methoxy benzimidazole (40 g) were dissolved in 95% ethanol (400 ml). To this sodium hydroxide solution (16 g of sodium hydroxide dissolved in 40 ml of water) was added and refluxed for 2 hours. The sodium chloride formed was filtered off and the solution was concentrated to residue. The residue was then recrystallised from 70% methanol (60 ml) at 50-55° C., chilled to −5 to 0° C. and maintained for 2 hours. The solid was filtered and dried at 40-45° C. under vacuum to yield 5-methoxy-2-[[(4-methoxy-3,5-dimethyl-2-pyridinyl)-methyl)thio]-1H-benzimidazole Form I (21.0 g).

Example 3

Preparation of 5-methoxy-2-[[(4-methoxy-3,5-dimethyl-2-pyridinyl)-methyl)thio]-1H-benzimidazole Form I 2-chloromethyl-3,5-dimethyl-4-methoxy pyridine hydrochloride (100 g) and 2-mercapto-5-methoxy benzimidazole (80 g) were dissolved in 95% ethanol (800 ml). To this sodium hydroxide solution (32 g of sodium hydroxide dissolved in 80 ml of water) was added and refluxed for 2 hours. The sodium chloride formed was filtered off and the solution was concentrated to residue. The residue was then dissolved in methylene chloride (120 ml) and stripped off methylene chloride with ethyl acetate (40 ml). Further ethyl acetate (160 ml) was added and heated to dissolve at 50-55° C., cooled to room temperature, chilled to −5 to 0° C., maintained for 1 hour. The solid was filtered and dried at 40-45° C. under vacuum to yield 5-methoxy-2-[[(4-methoxy-3,5-dimethyl-2-pyridinyl)-methyl)thio]-1H-benzimidazole Form I (47.0 g).

Example 4

Preparation of 5-methoxy-2-[[(4-methoxy-3,5-dimethyl-2-pyridinyl)-methyl)thio]-1H-benzimidazole Form II 2-hydroxymethyl-3,5-dimethyl-4-methoxy pyridine hydrochloride (300 g) was charged to dichloromethane (1770 ml) and cooled to 15-20° C. Thionyl chloride (240 g) was added slowly at 15 to 20° C. and the contents were stirred at 25 to 30° C. for 1 hour. After reaction completion, water (300 ml) was added at 15 to 20° C. and allowed to attain 25 to 30° C. To this reaction mass 2-mercapto-5-methoxy benzimidazole (252 g) and tetrabutyl ammonium bromide (6 g) was added, and the pH of the reaction mass was adjusted to 10.0 to 10.5 at 5 to 15° C. using 30% sodium hydroxide solution and stirred for 2 hours at 15 to 20° C. maintaining pH 10.0-10.5. After reaction completion the dichloromethane layer was separated and the aqueous layer was extracted with dichloromethane (370 ml×2). The dichloromethane layer was then washed with water until the pH of the aqueous layer was 7.0 to 7.5, dried over sodium sulphate and partially concentrated at temperature below 50° C. under vacuum. Ethyl acetate (240 ml) was added and stripped off to remove traces of dichloromethane, further ethyl acetate (800 ml) was added and heated to 50 to 60° C., cooled to room temperature, chilled to 10 to −5° C. and maintained for 1 hour. The product was then filtered, washed with chilled ethyl acetate (200 ml). The product was then dried at 30 to 35° C. to yield 5-methoxy-2-[[(4-methoxy-3,5-dimethyl-2-pyridinyl)-methyl)thio]-1H benzimidazole form II (392 g, 80.6% yield).

Example 5

Preparation of Potassium Salt of Esomeprazole

Toluene (500 ml) was charged followed by D-(−)-diethyl tartrate (19.0 g), titanium (IV) isopropoxide (13.0 g), stirred for 15 minutes. To this water was charged up to 0.4% based on the moisture content of the reaction mass. The reaction mass was stirred for 30 minutes at 25-30° C. to form a chiral titanium complex. Further, 5-methoxy-2-[[(4-methoxy-3,5-dimethyl-2-pyridinyl)-methyl]thio]-1H-benzimidazole form II (100 g) was charged to the complex and the contents were heated to 70° C. over a period of 1 hour and maintained at 70-75° C. for ½ hour. The reaction mass was then cooled to 10-15° C., cumene hydroperoxide (115 g) was slowly added at 10-15° C. over a period of 3 hours. After reaction completion methanolic potassium hydroxide solution (20 g of potassium hydroxide dissolved in 200 ml of methanol) was added to the reaction mass at 10-15° C., the contents were stirred at 25-30° C. for 2 hours and chilled to 10° C. The precipitated product was filtered under nitrogen atmosphere, washed with toluene (150 ml).

The so obtained esomeprazole potassium salt was purified by dissolving in acetone (2000 ml) at 50-55° C., clarified over hyflo then concentrated under vacuum and stripped off with methanol (165 ml) to 125 ml stage. To this methanol (200 ml) was charged, chilled to 10-15° C. and stirred for 2 hours. The resulting solid was filtered under nitrogen atmosphere and washed with chilled methanol (80 ml). The product was then dried under vacuum at 40-45° C. to yield potassium salt of esomeprazole (66.6 g, 57% yield, 99.5% purity, 99.79% enantiomeric purity).

Example 6

Preparation of Potassium Salt of Esomeprazole

Toluene (180 ml) was charged followed by D-(−)-diethyl tartrate (11.4 g), titanium (IV) isopropoxide (7.8 g), stirred for 15 minutes. To this water was charged up to 0.4% based on the moisture content of the reaction mass. The reaction mass was stirred for 30 minutes at 25-30° C. to form a chiral titanium complex. Further, 5-methoxy-2-[[(4-methoxy-3,5-dimethyl-2-pyridinyl)-methyl]thio]-1H-benzimidazole form I (60.0 g) was charged to the complex and the contents were heated to 70° C. over a period of 1 hour and maintained at 70-75° C. for ½ hour. The reaction mass was then cooled to 10-15° C., cumene hydroperoxide (69.0 g) was slowly added at 10-15° C. over a period of 3 hours. After reaction completion methanolic potassium hydroxide solution (12.0 g of potassium hydroxide dissolved in 120.0 ml of methanol) was added to the reaction mass at 10-15° C., the contents were stirred at 25-30° C. for 2 hours and chilled to 10° C. The precipitated product was filtered under nitrogen atmosphere, washed with toluene (90 ml).

The so obtained esomeprazole potassium salt was purified by dissolving in acetone (1200 ml) at 50-55° C., clarified over hyflo then concentrated under vacuum and stripped off with methanol (100 ml) to 75 ml stage. To this methanol (120 ml) was charged, chilled to 10-15° C. for 2 hours, filtered under nitrogen atmosphere and washed with chilled methanol (50 ml). The product was then dried under vacuum at 40-45° C. to yield potassium salt of esomeprazole (35 g, 50% yield, 99.69% purity, 99.82% enantiomeric purity).

Example 7

Preparation of Esomeprazole Magnesium Dihydrate Form A

Methanol (50 ml), potassium salt of esomeprazole (35 g) were charged and maintained at 25-30° C. for 10 minutes. To this methanolic magnesium chloride hexahydrate solution (8.1 g of magnesium chloride hexahydrate dissolved in 40 ml of methanol) was added over a period of 1 hour at 25-30° C. The contents were then heated to 40-45° C., maintained for 1 hour, chilled to 0-5° C., maintained for 15 minutes. The insolubles were filtered and washed with methanol (15 ml), methanol distilled off under vacuum at 45-50° C. to 70 ml stage and cooled to 25-30° C. To this water (60 ml) and acetone (185 ml) mixture was added, stirred for 1 hour at 25-30° C., chilled to 0-5° C., maintained for 30 minutes, filtered the material under nitrogen atmosphere, washed with ethyl acetate (50 ml) and immediately dried at 60-65° C. under vacuum to yield the titled compound (21.4 g, 63% yield, water content of 5.7%).

Example 8

Preparation of Esomeprazole Magnesium Dihydrate Form A

Ethanol (35 ml), potassium salt of esomeprazole (25 g) were charged and maintained at 25-30° C. for 10 minutes. To this, ethanolic magnesium chloride hexahydrate solution (5.8 g of magnesium chloride hexahydrate dissolved in 28.5 ml of ethanol) was added over a period of 1 hour at 25-30° C. The contents were then heated to 40-45° C. and maintained for 1 hour, chilled to 0-5° C., maintained for 15 minutes. The insolubles were filtered and washed with ethanol (15 ml) ethanol was partially distilled under vacuum at 45-50° C. and cooled to 25-30° C. To this, water (43 ml) and acetone (132 ml) mixture was added, stirred for 1 hour at 25-30° C. and chilled to 0-5° C., maintained for 30 minutes, the solid was filtered under nitrogen atmosphere, washed with ethyl acetate (35 ml) and dried at 60-65° C. under vacuum to yield the titled compound (14.6 g, 61% yield, water content of 5.5%).

Example 9

Preparation of Esomeprazole Magnesium Dihydrate Form A

Methanol (50 ml), potassium salt of esomeprazole (35 g) were charged and maintained at 25-30° C. for 10 minutes. To this methanolic magnesium chloride hexahydrate solution (8.1 g of magnesium chloride hexahydrate dissolved in 40 ml of methanol) was added over a period of 1 hour at 25-30° C. The contents were then heated to 40-45° C. and maintained for 1 hour, chilled to 0-5° C., maintained for 15 minutes. The insolubles were filtered and washed with methanol (15 ml), distilled off methanol under vacuum at 45-50° C. to 80 ml stage and cooled to 25-30° C. To this, water (80 ml) and ethyl acetate (185 ml) mixture was added, stirred for 1 hour at 25-30° C., chilled to 0-5° C., maintained for 2 hours, the solid was filtered under nitrogen atmosphere, washed with ethyl acetate (50 ml) and dried at 60-65° C. under vacuum to yield the titled compound (21.1 g, 62% yield, water content of 5.7%).

It will be appreciated that the invention may be modified within the scope of the appended claims.

Figure 3:
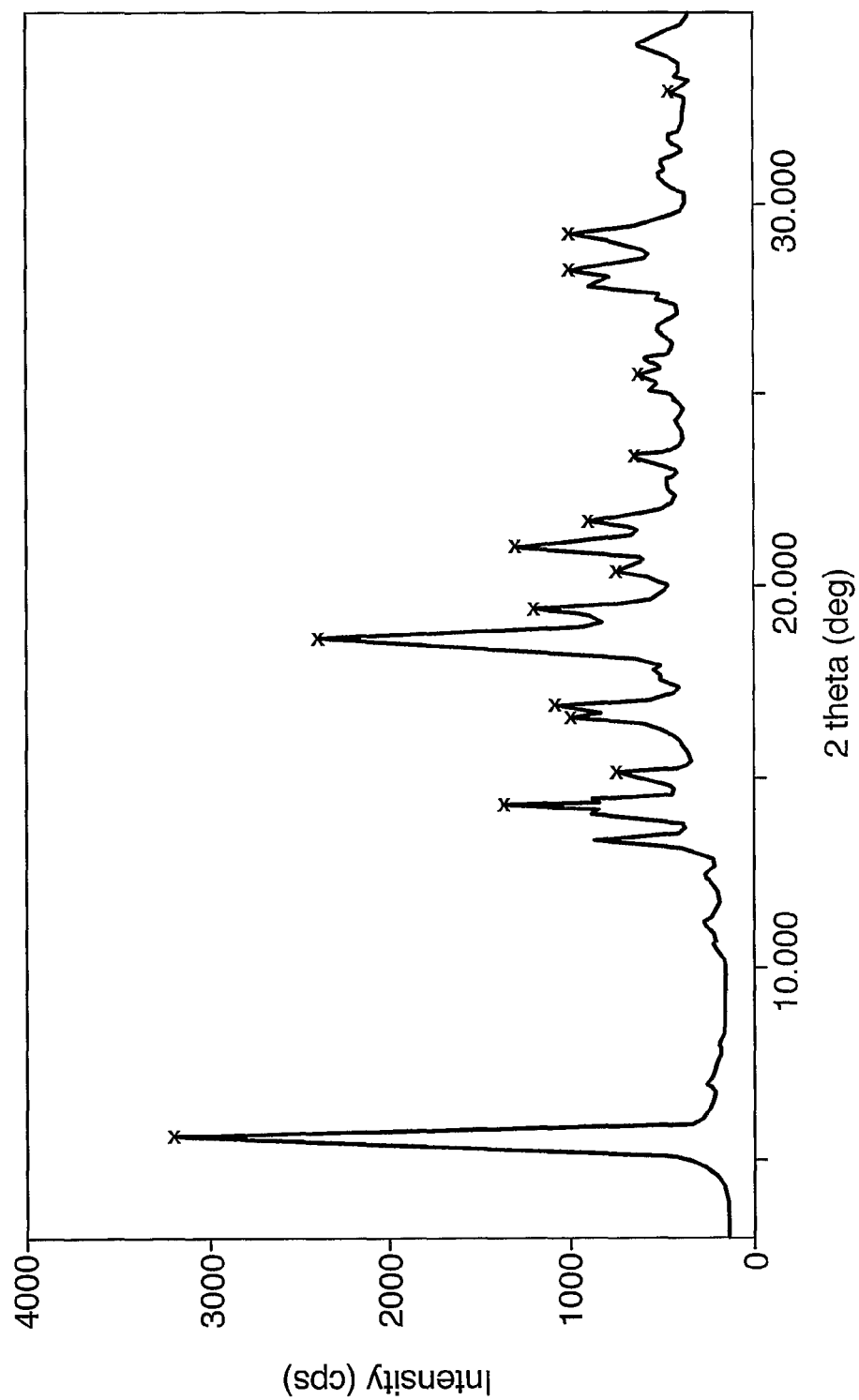
FIG. 3 shows the X-ray powder diffractogram of Form A of esomeprazole magnesium dihydrate.

The invention claimed is:

1. A process for preparing Form A of (S)-5-methoxy-2-[[(4-methoxy -3,5-dimethyl-2-pyridinyl)-methyl]sulfinyl]-1H-benzimidazole magnesium dihydrate comprising crystallizing or recrystallizing crude (S)-5-methoxy-2-[[(4-methoxy -3,5-dimethyl-2-pyridinyl)-methyl]sulfinyl]-1H-benzimidazole magnesium dihydrate in the presence of ethyl acetate, wherein Form A of )-5-methoxy-2-[[(4-methoxy-3,5-dimethyl-2-pyridinyl)-methyl]sulfinyl]-1H-benzimidazole magnesium dihydrate has the XRPD pattern as shown in FIG. 3.

2. The process according to claim 1, wherein the crude (S)-5-methoxy-2-[[(4-methoxy-3,5-dimethyl-2-pyridinyl)-methyl]sulfinyl]-1H-benzimidazole magnesium dihydrate is formed by reacting a salt of (S)-5-methoxy-2-[[(4-methoxy-3,5-dimethyl-2-pyridinyl)-methyl]sulfinyl]-1H-benzimidazole with a magnesium source and in the presence of an organic solvent.

3. The process according to claim 2, wherein the salt of (S)-5-methoxy-2[[(4-methoxy-3,5-dimethyl-2-pyridinyl)-methyl]sulfinyl]-1H-benzimidazole is formed via conversion of (S)-5-methoxy-2-[[(4-methoxy-3,5-dimethyl-2-pyridinyl)-methyl]sulfinyl]-1H -benzimidazole.

4. The process according to claim 3, wherein the salt is an alkali metal salt.

5. The process according to claim 4, wherein the alkali metal salt is the potassium salt.

6. The process according to claim 5, wherein the (S)-5-methoxy-2-[[(4-methoxy-3,5-dimethyl-2-pyridinyl)-methyl]sulfinyl]-1H-benzimidazole is converted to the potassium salt in the presence of a potassium source.

7. The process according to claim 6, wherein the potassium source is methanolic potassium hydroxide, methanolic potassium methoxide or ethanolic potassium hydroxide.

8. The process according to claim 1, wherein the crystallizing or recrystallizing is initiated by the addition of a solvent comprising ethyl acetate to the crude (S)-5-methoxy-2-[[(4-methoxy-3,5-dimethyl-2-pyridinyl) -methyl]sulfinyl]-1H-benzimidazole magnesium dihydrate.

* * * * *

UNITED STATES PATENT AND TRADEMARK OFFICE
CERTIFICATE OF CORRECTION

PATENT NO.       : 8,394,963 B2                                               Page 1 of 1
APPLICATION NO.  : 12/527967
DATED            : March 12, 2013
INVENTOR(S)      : Rao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 630 days.

Signed and Sealed this
First Day of September, 2015

Michelle K. Lee
*Director of the United States Patent and Trademark Office*